(12) United States Patent
Garman et al.

(10) Patent No.: US 6,846,668 B1
(45) Date of Patent: Jan. 25, 2005

(54) MICROFABRICATED CELL INJECTOR

(75) Inventors: Andrew J. Garman, Cheshire (GB); David J. Scanlon, Cheshire (GB); John Dodgson, Surrey (GB); John Ea Shaw, Middlesex (GB); David Brennan, Middlesex (GB); Anthony R. Corless, Surrey (GB); Christopher M. Turner, Middlesex (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/763,825
(22) PCT Filed: Oct. 7, 1999
(86) PCT No.: PCT/GB99/03330
§ 371 (c)(1), (2), (4) Date: Apr. 30, 2001
(87) PCT Pub. No.: WO00/20554
PCT Pub. Date: Apr. 13, 2000

(30) Foreign Application Priority Data

Oct. 8, 1998 (GB) .............................................. 9821833
Aug. 7, 1999 (GB) .............................................. 9918614

(51) Int. Cl.[7] ......................... C12M 3/00; C12M 15/89
(52) U.S. Cl. ................. 435/285.1; 435/455; 435/288.5; 435/287.2
(58) Field of Search .............................. 435/285.1, 455, 435/470, 288.5, 287.2; 600/345

(56) References Cited

U.S. PATENT DOCUMENTS

| 5,225,750 A | 7/1993 | Higuchi et al. |
| 5,296,375 A | 3/1994 | Kricka et al. |
| 5,427,946 A | 6/1995 | Kricka et al. |
| 5,457,041 A | 10/1995 | Ginaven et al. |
| 5,482,598 A | 1/1996 | Isaka et al. |
| 5,716,852 A | 2/1998 | Yager et al. |

FOREIGN PATENT DOCUMENTS

| CA | 2 230 653 | 8/1999 |
| WO | 91/05519 | 5/1991 |
| WO | 93/22053 | 11/1993 |
| WO | 96/10630 | 4/1996 |
| WO | 98/00231 | 1/1998 |
| WO | 98/04909 | 2/1998 |
| WO | 98/28406 | 7/1998 |
| WO | 98/29736 | 7/1998 |

OTHER PUBLICATIONS

Schober et al., "Systemintegration of microsystems . . . ," Microsystem Technologies, vol. 4, pp. 35–39 (1997).
Peled, Nina, "Design and implementation . . . ," Pure & Appl. Chem., vol. 68, No. 10, pp. 1837–1841 (1996).
Blankenstein et al, "Modular concept of a . . . ," Biosensors & Bioelectronics, vol. 13, No. 3–4, pp. 427–438 (1998).
Kricka, L., "Miniaturization of analytical systems," Clinical Chemistry, vol. 44, No. 9, pp. 2008–2014 (1998).
Fu et al., "A microfabricated fluorescence," Nature Biotechnology, vol. 17, pp. 1109–1111 (1999).

Primary Examiner—William H. Beisner
(74) Attorney, Agent, or Firm—Nixon & Vanderhye

(57) ABSTRACT

The microfabricated cell injector having an injection wall and a cell injection needle projecting from the wall for piercing cells suspended in a fluid. The needle is held within a housing defined by the internal surfaces of the microfabricated cell injector. The housing has an inlet for suspended cells to enter and an outlet for cells to exit via the cell injection needle. A cell propulsion device is provided for impelling cells towards the needle such that, in use, cells suspended in the fluid are impelled towards the injection wall by the injection needle.

9 Claims, 17 Drawing Sheets

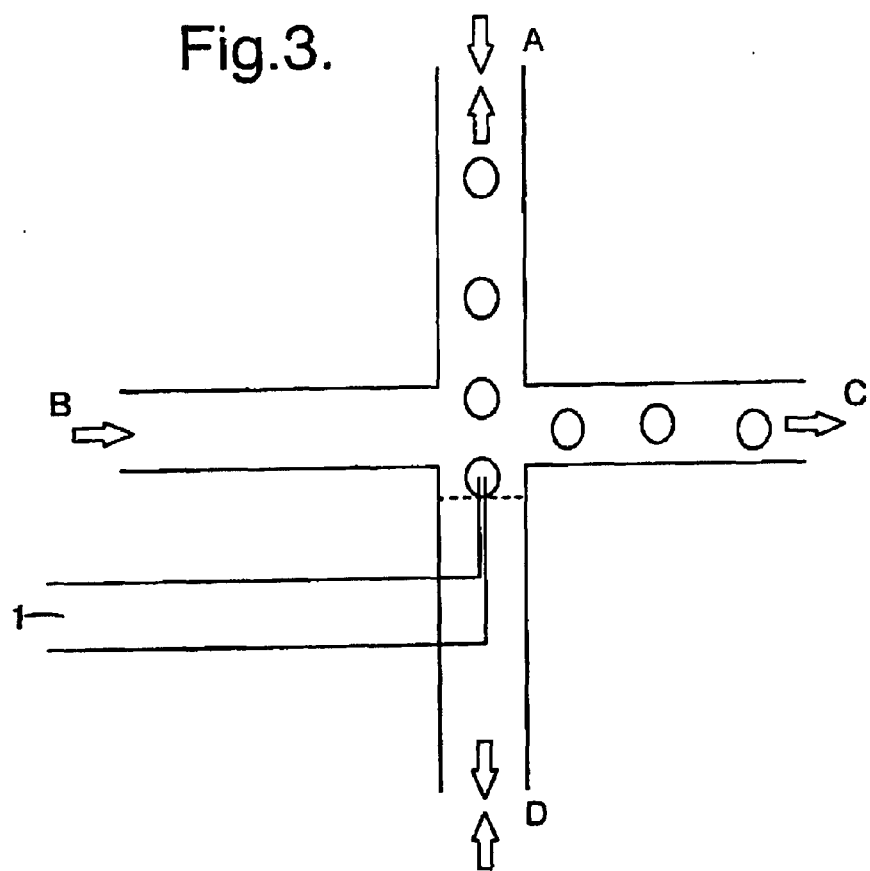
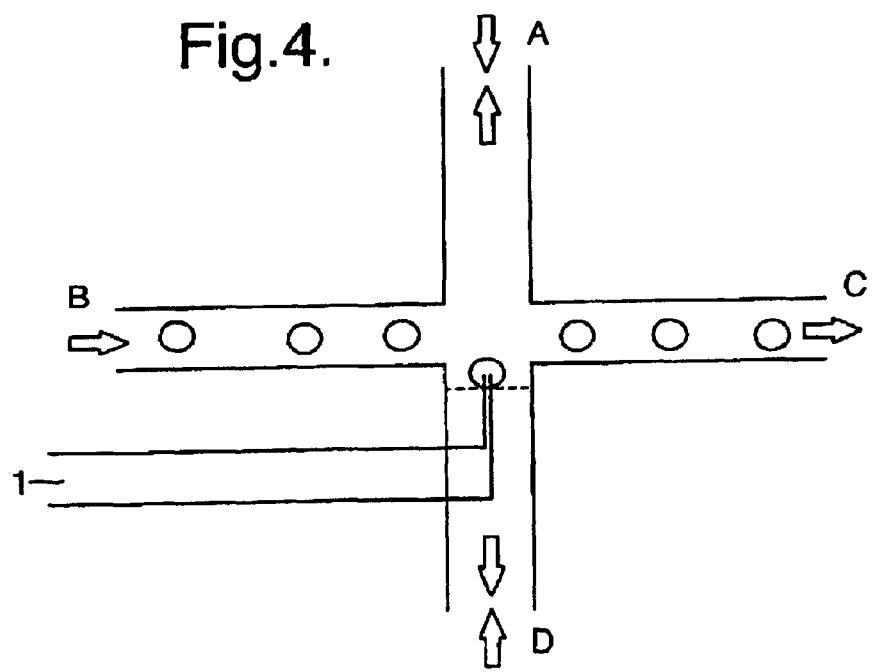

▽ =Injection area

Fig.10.
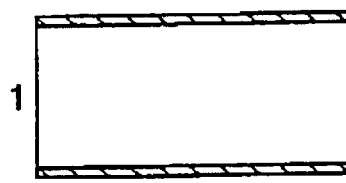
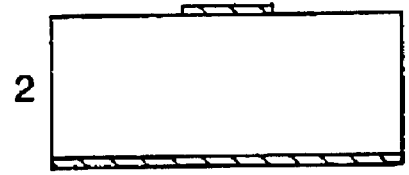
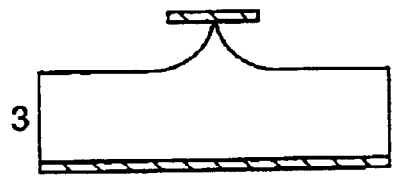
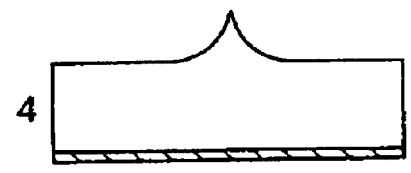
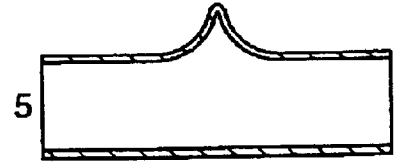
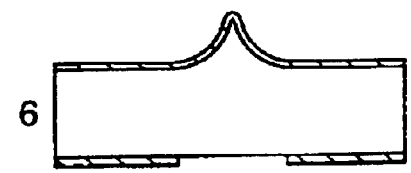
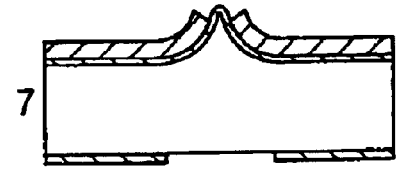
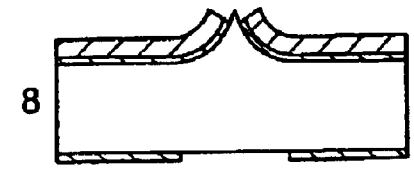
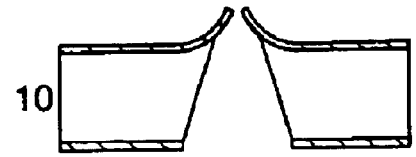

Fig.11b.
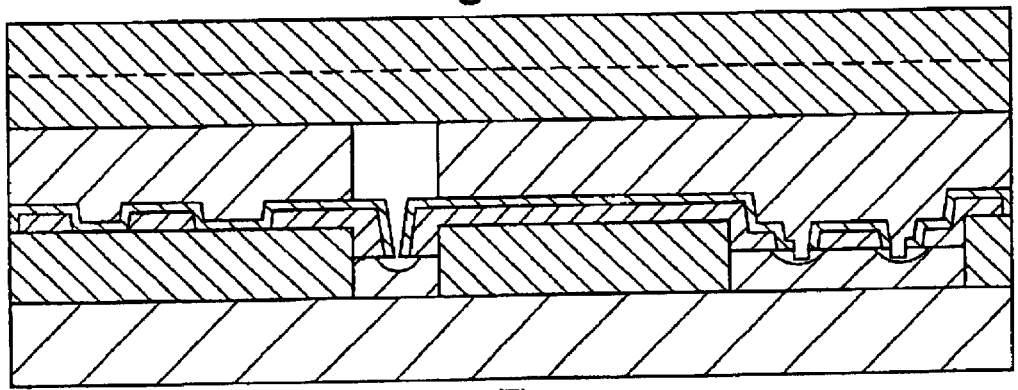
(7)
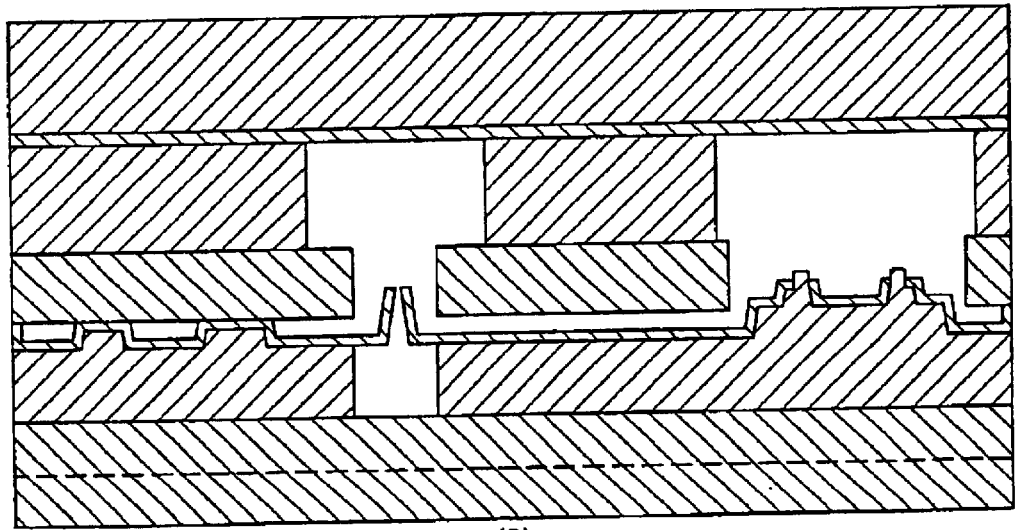
(8)

Fig. 12b.
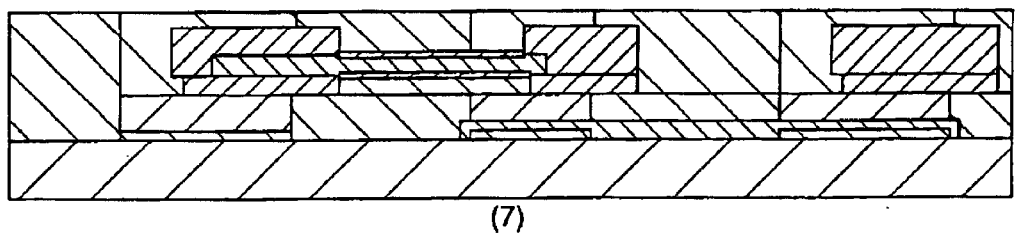
(7)
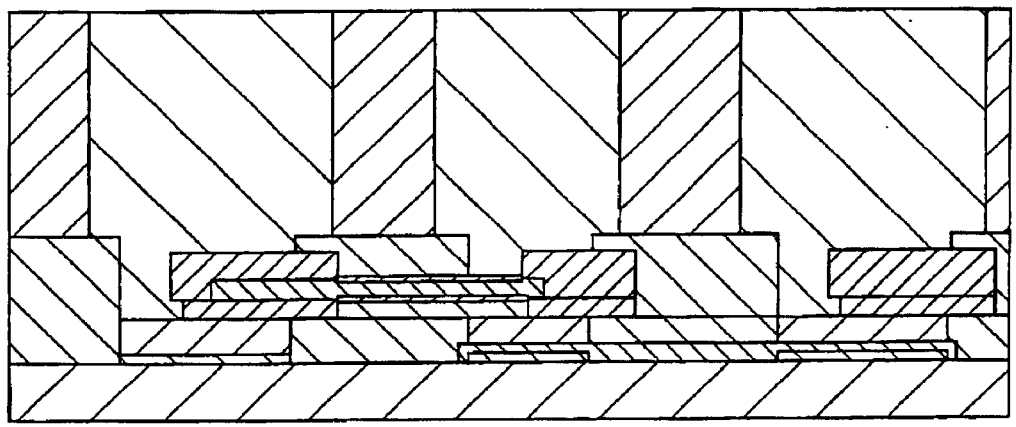
(8)
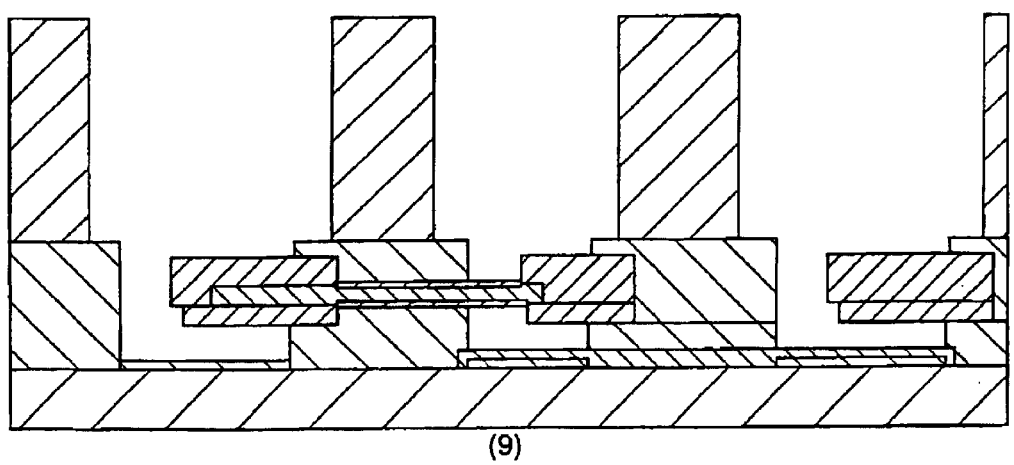
(9)

Fig.12c.
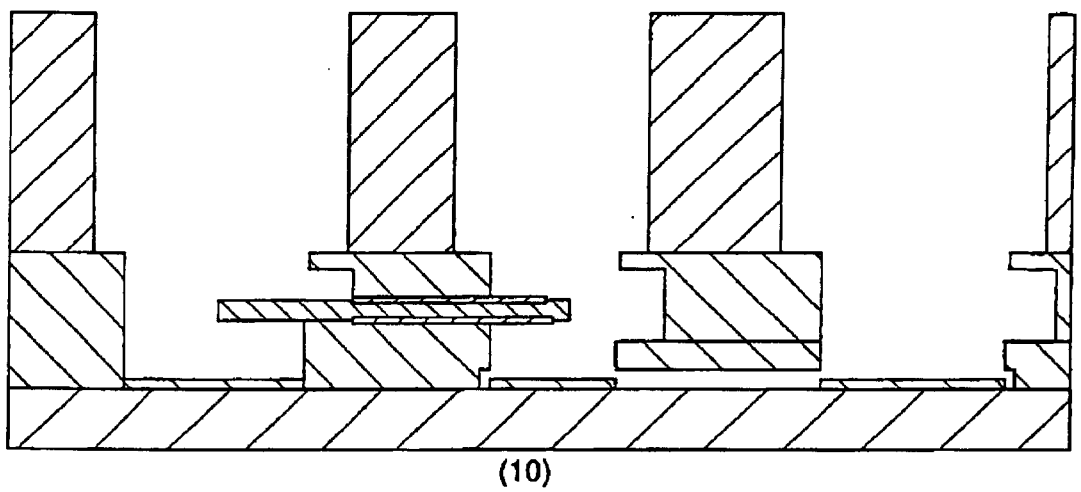
(10)
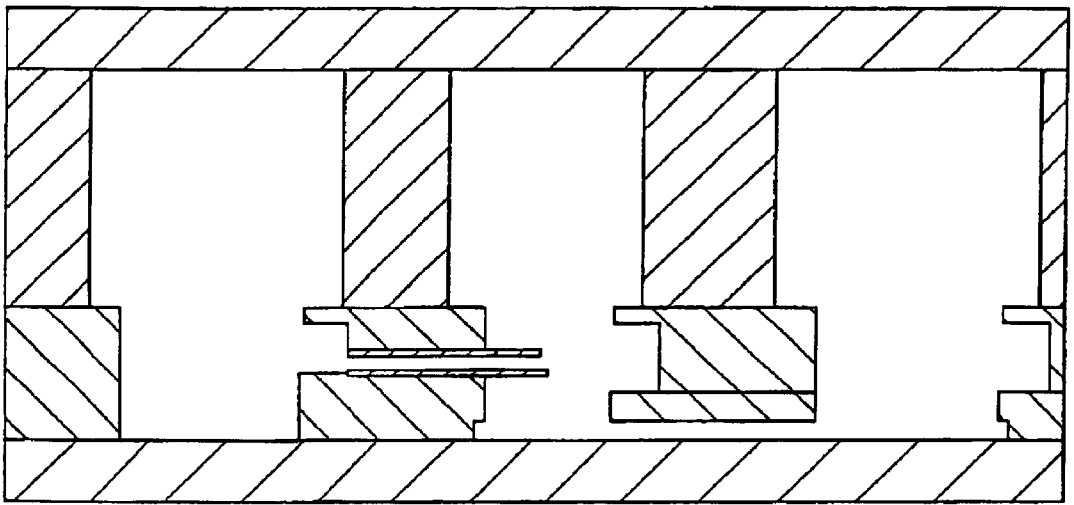
(11)

MICROFABRICATED CELL INJECTOR

The invention relates to a device for, and method of, injecting small articles, in particular cells. More particularly, but not exclusively, the invention relates to an automated device for and method of injection of large numbers of cells. The invention also includes use of such a device, specifically in fields where low throughput of cell injection from current techniques has meant that such uses have not been viable.

BACKGROUND OF THE INVENTION AND SUMMARY OF THE INVENTION

Injection of cells is currently only a viable technique in a limited number of fields, for example in vitro fertilisation, and currently is carried out manually and individually on each cell. It requires a high level of skill and an experienced operator can only inject in the order of one cell per minute. There are many other fields that would benefit from cell injection of macromolecules, genes, chromosomes, organelles, or any other substance desired to be injected into a cell were it possible to achieve this on a large numbers of cells. Gene therapy, biotechnology, life sciences research, diagnostics, pharmaceutical and agrochemical research are among many fields that would benefit from a more facile high throughput cell injection method.

Currently using manual techniques the cells are suspended in solution and each cell is individually injected by fixing a cell into position by the operator "sucking" the cell onto the end of a narrow pipette. Whilst watching the operation through a microscope the operator then inserts a needle into the cell. Once the injection is made the needle is retracted manually and the cell released, then the next cell is injected and so on. In addition variations of this basic manual technique are available such as, for example, for injecting cells which are attached to a dish as a monolayer. The cost of injecting a small number of cells is expensive and means that microinjection of cells is not a technique used widely in the pharmaceutical or agrochemical research.

We have devised of a device in which a large numbers of cells (hundreds, thousands or millions) may be micro-injected with minimal operator involvement by use of a microfabricated device which impels cells onto an injection needle.

Microfabrication techniques are generally known in the art using tools developed by the semiconductor industry to miniaturise electronics and it is possible to fabricate intricate fluid systems with channel sizes as small as a micron. These devices can be mass-produced inexpensively and are expected to soon be in widespread use, for example, in simple analytical tests. See, e.g., Ramsey, J. M. et al. (1995), "Microfabricated chemical measurement Systems," Nature Medicine 1:1093–1096; and Harrison, D. J. et al (1993), "Micromachining a miniaturized capillary electrophoresis-based chemical analysis system on a chip," Science 261:895–897.

Devices made by micromachining planar substrates have been made and used for chemical separation, analysis, and sensing. See, e.g., Manz, A. et al. (1994), "Electroosmotic pumping and electrophoretic separations for miniaturized chemical analysis system," J. Micromech. Microeng. 4:257–265.

We have been able to construct a microfabricated needle onto which cells may be impelled towards so that the needle pierces the cell and material may be injected or extracted from the cell.

We present as a first feature of the invention a microfabricated cell injector comprising an injection wall and projecting from the injection wall a cell injection needle, such that in use cells suspended in a fluid are impelled towards the injection wall and pierced by the injection needle whereupon material is (1) injected into the cell, (2) extracted from the cell, or (3) injected into the cell and then extracted from the cell the steps being in any order and any number of times.

We have also found that by careful arrangement of channels (microfluidic channels) formed within a microfabricated device a conduit is formed through which the flow of cells in a suspension may be controlled to an extent that cells may be injected by impelling them onto an injection needle individually.

We disclose as a further feature of the invention a microfabricated cell injector comprising an internal surface defining a conduit, which in use transports cells suspended in a fluid, the conduit having an inlet and an outlet, the conduit further comprising a cell injection needle, such that, in use cells enter the injector via the inlet, are moved along the conduit and are pierced by the cell injection needle whereupon material is (1) injected into the cell, (2) extracted from the cell, or (3) injected into the cell and then extracted from the cell the steps being in any order and any number of times, and the cells are then, optionally, moved to the outlet.

A further feature of the invention is a method for the microinjection of cells which method comprises passing a suspension of cells in a fluid through a conduit comprising a cell injection needle, the cells thereby being pierced by the injection needle and material is: (1) injected into the cell (2) extracted from the cell or (3) injected into the cell and then extracted from the cell the steps being in any order and any number of times; as the cells pass through the conduit.

It should be understood that the arrangement, type and dimensions of the device and the components therein will vary according to the use or application, as will become apparent. It is generally preferred that the microfabricated conduit only allows a single cell to be impelled upon a single injection needle at any one time.

In this disclosure, the term "microfabricated" includes, for example, devices capable of being fabricated on glass, plastic, silicon or any other suitable material. Suitable microfabrication techniques are those readily available to those practising the art of microfabrication and include such methods as LIGA, thermoplastic micropattern transfer, resin based microcasting, micromolding in capillaries (MIMIC), wet isotropic and anisotropic etching, laser assisted chemical etching (LACE), and reactive ion etching (RIE), or other techniques known within the art of microfabrication. In the case of silicon microfabrication, larger wafers will accommodate a plurality of the devices of this invention in a plurality of configurations. A few standard wafer sizes are 3"(7.5 cm), 4"(10 cm), 6"(15 cm), and 8"(20 cm). Application of the principles presented herein using new and emerging microfabrication methods or materials is within the scope and intent of the invention.

The injection needle has a diameter of dimensions comparable with the dimension of the cells to be injected, for example between 1% and 50% of the cell diameter, preferably between 5% and 30%. Typical cell diameters are from 10 microns to 50 microns, but will vary according to the cell origin and type. The walls of the injection needle when hollow may be from 1 micron thick and may be as narrow as 0.1 micron thick at the point of the needle. Where the injection needle has a hollow tip this is connected to a microfluidic channel which is able to deliver to the injection needle tip the material for injection. Preferably the injection needle is fixed in the device relative to the walls of the microfluidic channels which form the conduit such that it projects and injection is achieved by moving the cells on and off the injection needle, rather than by moving the injection needle into and out of the cell. Preferably the injection needle is positioned on a surface of the microfluidic channel, which we term the "injection wall", see for example FIG. 1. The injection wall forms part of the "housing" for the needle which may be simply an integral part of the conduit or may be a distinct aspect which forms a suitable receptacle for receiving/positioning/holding the cell prior to injection. The length and shape of the injection needle that is exposed above the injection wall will determine the "injection depth", that is the depth to which the injection needle will penetrate the cell. This depth will depend on the cell type, the design of the needle, and the application. In particular, it will depend on the cellular compartment that it is desired to inject into. For example, for injection into the cytoplasm, the injection depth could be in the order of 1 micron, for example 1 to 5 microns; whereas, for an injection into the nucleus, the injection depth will need to be greater, for example 3–10 microns. Given a knowledge of the cell type, it will be possible for the skilled bioscientist to select a device with the appropriate injection depth.

Preferably the needle is hollow and substantially circular in cross section, the external diameter of the needle continuously decreasing as it projects from the base of the needle to its tip, the tip being less than 25 microns, preferably less than 5 microns, in diameter. As a feature of the invention we present use of the above described needle in the piercing and injecting of material into, or extracting material from, cells.

The injection wall surrounding the immediate area of the injection needle may be permeable to the medium in which the cells are contained, but impermeable to the passing of cells. In certain orientations of the device permeable walls are preferred and allow the passing of the cell medium through the injection wall, facilitating the movement of the cell towards the injection needle. The permeability of the wall may be achieved by one or a small number of orifices positioned around the needle, preferably in a symmetrical fashion. It will be clear that a large number of designs could in principle achieve the aim of forcing the cell onto the needle and these are incorporated into the invention. The injection wall may optionally itself be charged to attract the cell towards the injection needle, or reverse charged to expel the cell from the injection needle. Alternatively the charge may alternate to impel the cell onto the needle and then to expel it. The injection wall may be flat or any other shape to accommodate the cell whilst it is on the injection needle.

BRIEF DESCRIPTION OF THE DRAWINGS

Embodiments of the invention are now described, by way of examples only and with reference to the Figures, in which:

The invention is described in more detail below in the following non-limiting figures.

FIGS. 3 and 4 are diagrammatical representations of an injection system, enabling automatic delivery and removal of a cell;

DETAILED DESCRIPTION OF PREFERRED EMBODIMENTS

Figure 1:
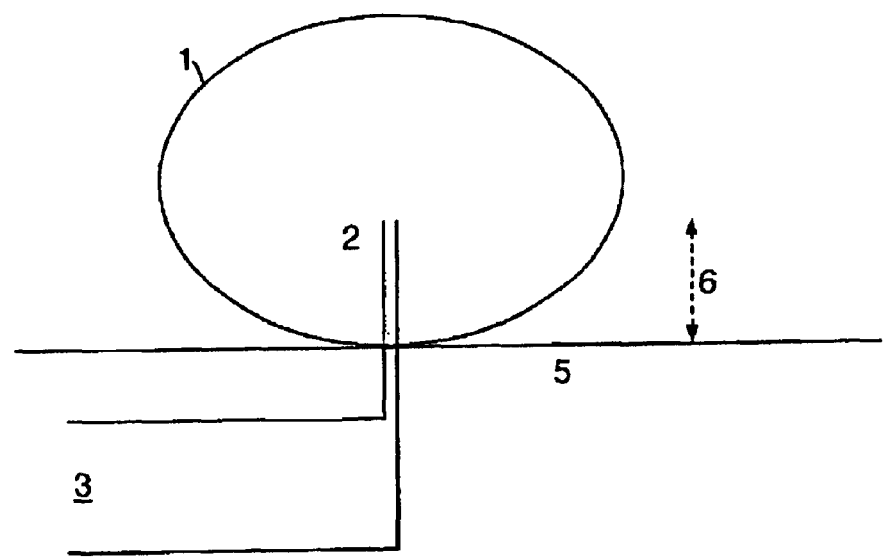
FIG. 1 is a diagrammatical cross-sectional view of a needle injecting a small article, such as a cell.

Referring to the figures generally, and specifically to FIG. 1, the depth of entry 6 of the injection needle 2 into the cell 1 is defined by the distance the cell may travel before it is stopped at the cell injection wall 5. Material 3 may be injected into the cell by pulsed injection when the cell is in position, or by continuous flow where the time the cell is spent on the injection needle is regulated.

Figure 2:
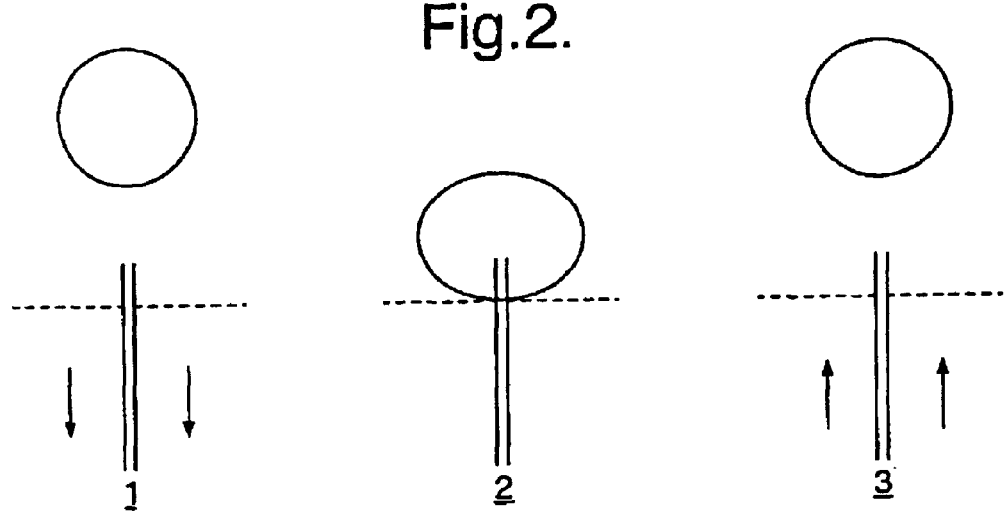
FIG. 2 shows diagrammatically views of a cell approaching, impinging and being removed from a needle.

FIG. 2—Shows one alternative method for impelling the cell onto the injection needle and removal once injection has taken place. The cell is impelled onto the injection needle 1 and 2 by a passive force, i.e. the liquid and cell moves, or an active force, i.e. where the cell moves. Movement of the cell onto the injection needle is eased by providing a permeable cell injection wall for the cell suspending liquid to pass through. The cell is removed from the injection needle by providing an opposite active or passive force 3.

Figure 7:
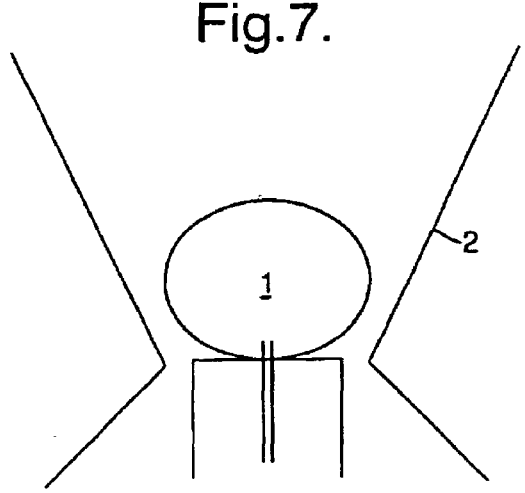
FIG. 7 is a diagrammatical view of a needle housing.

FIG. 7—Shows an alternative arrangement for the injecting wall is at the base of the needle and the narrowing channel which supports the cell 1 during injection is the housing.

The injection needle may be a fabricated separately from the microfabricated conduit and inserted during manufacture into the device. Alternatively the injection needle is fabricated during the manufacture of the conduit and the injection needle formed as a simple projection from the surface of the injection wall, see for example FIG. 8.

The design of the needle is conveniently conventional that is comprising a single hollow tube, preferably sharp at the point and optionally widening towards the base. However, other structures are included. We include structures where the penetration of the cell and the injection of fluid are achieved by different parts of the structure. For example, the point of the needle may be solid and injection of fluid carried out by means of side channels. Alternatively, the needle may be a simple point made out of a porous material, the injected material entering the cell by means of the pores. Alternatively, the needle is a solid point for piercing the cell, preferably along one side of the needle a groove, and the material present in the suspension fluid is allowed to flow into the cell.

As an alternative to a cell piercing needle as described above a non-cell piercing needle or area may be used in which the cell is held against and from which a membrane-opening chemical or force is applied.

The choice of needle design will depend on factors such as the size of the cell, the type of cell, the desired efficiency of injection (measured as the percentage of cells injected or the percentage of injected material that is injected).

The injection needle is conveniently an essentially rigid structure, that is it does not move significantly with respect to the rest of the device. However, depending on the microfabrication approach employed, it may be convenient for the needle to be flexible, i.e. movement is allowed in the direction of the needle axis. Optionally this flexibility may be exploited to augment the needle penetration pressure, either due to the elasticity of the structure, or differences in hydrostatic pressure, or both.

Figure 9:
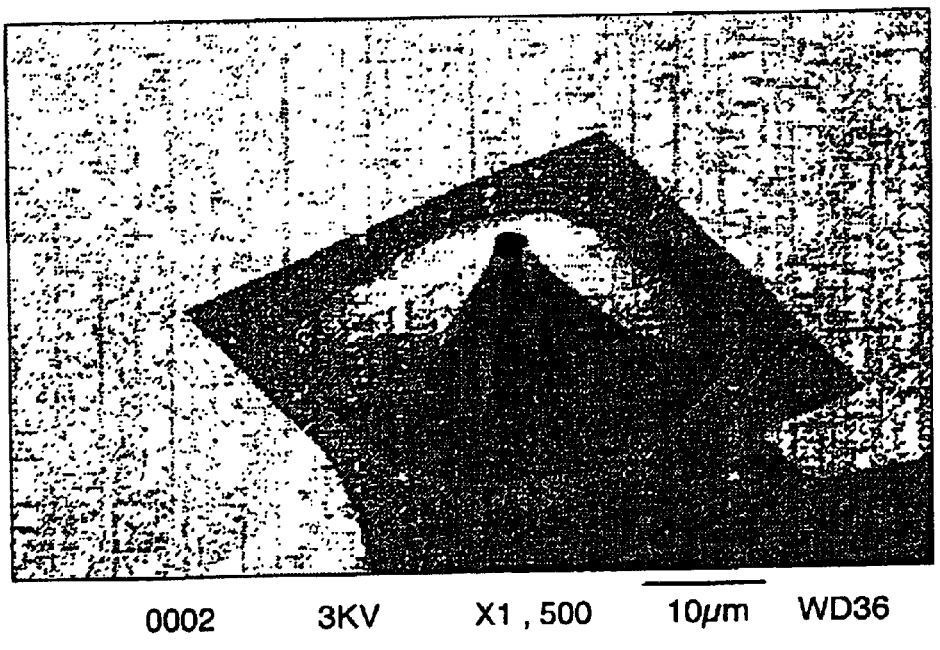
FIG. 9 is a photograph taken through an electron microscope of a cell injector needle.

FIG. 9—Is a photograph taken through an electron microscope of a cell injector needle, magnification ×1500, The needle is 2 microns at the top and the walls are 0.1 micron thick. The silicon slab is back-etched so that there is a hole right through the structure which is used for injection of material into the cell.

It is convenient for the channel that provides the driving force impelling the cells onto the needle to be defined in part by the plane in which the needle structure is fabricated.

The conduit may comprise any number of microfluidic channels within the device so as to form an opening for entrance of cells into the device and the conduit being in fluid communication with a second opening for cells to exit the device. The microfluidic channels may be of any suitable size and dimensions which allow cells suspended in a fluid to flow from the entrance to the exit via the cell injecting needle. Diameters of the microfluidic electrostatic field. Means of manipulating cells by various types of electric field are described in the literature, see for example R. Pethig and G. H. Markx, Trends in Biotechnology (1997) 15, 426-. Combinations of methods are also possible, for example, the cells may be delivered to the injection area of the device by passive flow and then impelled by an active force onto the injection needle.

The above cell movement methods are may also be used, optionally in combination, to remove the cell from the injection needle and to flow the cells away and out of the device.

Where the cells are manipulated onto or off the injection needle by passive flow, the injection wall may alternatively be constructed with holes or small channels therein, or is of a porous material, so that fluid can flow relatively unhindered through the wall. FIG. 2 illustrates an example of an arrangement capable of achieving this.

Figure 6:
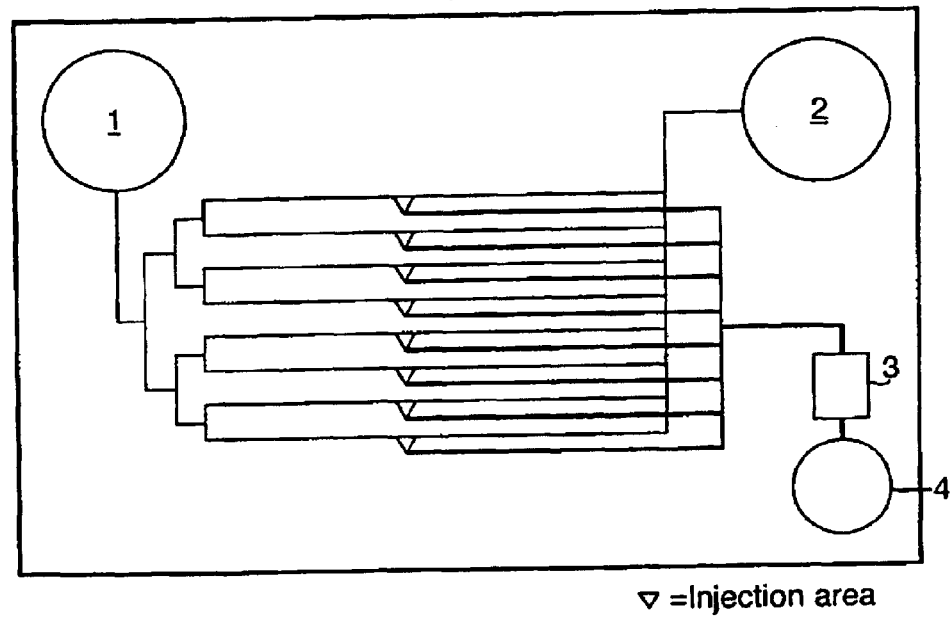
FIG. 6 is a diagrammatical view of a cell injector device having a number of cell injector units run in parallel.

By high throughput we mean that the invention can achieve a throughput substantially higher than conventional means and that numbers of cells in the orders of 100, for example 1,000 or 1 million, can be achieved in a convenient time period in the order of minutes or hours. In order to achieve the higher throughputs, the method optionally involves parallel processes, i.e. multiple devices are used in parallel and cells are flowed along a plurality of microfluidic channels such that they are impelled onto a plurality of injection needles, for example, one injection needle per channel. FIG. 6 shows such a device with 8 channels in parallel. A requirement of such devices, which we term "multi-channel" is that the inlets of the multiple injector units are connected to suitable channels to divide up the flow of cells from a cell sample reservoir, then, preferably, recombined after injection, and the material for injection is also divided up by suitable channels to provide material to each injection area.

Accordingly we disclose as the second feature of the invention a microfabricated device containing a plurality of cell injector units, each cell injector unit comprising a conduit or an internal surface defining a conduit for transporting cells suspended in a fluid, and having an inlet and an outlet, the conduit further comprising a cell injection needle, such that in use cells enter the injector via the inlet and are moved along the conduit, pierced by the injection channels may vary along the conduit but will typically range from 10 microns to 300 microns, preferably 30 microns to 100 microns.

Optionally the cells are accelerated onto the needle by means of a restriction in the microfluidic channel which increases the linear velocity of the cell. Alternatively the walls of the channel could be fashioned to compress the cell to assist with the injection.

Cells may be suspended in any fluid which is able to flow readily through microfluidic channels and not adversely harm the cells suspended within the fluid. Preferred fluids are buffered aqueous solutions, at physiological pH, optionally containing cell nutrients to preserve cell viability.

The method/device of the invention includes active propulsion of the cell onto the needle, in addition to or instead of the forces provided by movement of the cell suspension. By active propulsion we include provision of a pressure behind the cell (opposite side to the needle) by means of a deformable section of the channel wall, such deformation being achieve by externally applied pressure such as gas pressure, liquid pressure or mechanical pressure. We also include provision of a negative pressure ahead of the cell (same side as the needle) by the same or similar means. We also include an additional, optionally externally applied, positive or negative pressure pulse in the carrier liquid in which the cells are suspended. We also include other external forces such as magnetic or electrostatic fields acting on an appropriately derivatised cell suspension. Cells may be moved along the microfluidic channels and impelled onto the injection needle by any convenient means. Two broad categories are envisaged. Firstly is passive flow, where the carrier fluid containing the cells of interest is moved and the cells flow with it. The carrier fluid may be propelled by means of a mechanical pump, by applying a vacuum or pressure to one end of the channel, by gravity flow, by electro-osmosis or any other suitable means. Electro-osmosis, which may conveniently be achieved by the microfabrication of electrodes at the ends of the channels, the voltages between electrodes being controlled conveniently externally to achieve the desired fluid movements. Alternatively active flow may be employed where the cell is moved actively, i.e. independently of the carrier fluid by means of an external field, for example an needle whereupon material is injected into the cell or extracted, and then moved to the outlet, the respective inlets and outlets of the cell injecting units being each connected such that the cells are divided into each injector unit and, preferably, recombined after injection.

The injection material is any material that it is desired to inject into the cell. Most advantageously, this is material that cannot readily be taken up by the cell of interest by any other convenient means. In particular, the material for injection is a macromolecule in aqueous solution, for example a peptide, protein, nucleic acid or polysaccaharide, and analogues and conjugates thereof. Also the injection material may comprise particles, for example viruses, chromosomes, synthetic particles optionally containing or coated with a macromolecule of interest, spores, plasmids, cell organelles, vesicles, liposomes, micelles and emulsions. Optionally a label, for example a fluorescent label, may be added to the injection fluid to act as a marker to indicate that the injection is successful. Ideally the material is suspended or dissolved in a liquid, such as an aqueous buffer.

The arrangement of microfluidic channels to effect the method of the invention will depend on many factors such as the desired throughput and means of propelling cells.

FIG. 3—Is a diagram of a microfabricated cell injector with a conduit consisting of two channels crossing in opposing directions. Cells are impelled down channel A to D stepwise by an oscillating force which switches cell movement from A to D then D to A, the movement of cells from A to D being larger then the return movement and impelling a cell onto the injection needle 1. The smaller returning force D to A releases the cell from the injection needle after injection and places it in line with channel B to C. The cell is moved along B to C and then a force applied again to impel the next cell onto the injection needle in direction A to D.

In the case of passive flow and use of a porous injection wall, a convenient configuration is shown in FIG. 3. Here a stream of cells enters along channel A (at this point in the cycle there is no flow between arms B and C) and the leading cell becomes impaled on the injection needle. A "capture sensor" senses that a cell is captured and the flow is halted and the material for injection is injected. The flow is immediately reversed in a short pulse which dislodges the cell. The strength and duration of this pulse is selected such that the cell is delivered to the centre of the cross. Flow from arm B to arm C (the reverse is possible) is initiated and the cell is removed along arm C. The cycle then starts again with flow along channel A which capture the next cell, the said cycles being repeated until the desired number of cell have been injected.

Alternatively, cells may be introduced along arm B and moved along arm A, as is illustrated in FIG. 4.

FIG. 4—Shows an alternative arrangement of the microfabricated cell injector of FIG. 3 where the cells are moved along channel B to C in a stop/start motion where a cell placed in-line with channel A to D during the stop phase is impelled onto the injection needle by a force A to D and removed by a force D to A and placed back in line with the channel B to C and removed by the next movement in channel B to C.

Suitable capture sensors include a conductivity sensor that measures the conductivity or capacitance between the injection fluid and the carrier fluid. Conductivity changes when the needle penetrates the cell. Optionally, the change in impedance may be measured to detect a cell that is adhered to the needle but not actually penetrated by it. Alternatively, the capture sensor may take the form of a pressure transducer positioned near the point of capture such that capture causes a partial blockage of the flow in the pressure transducer and a change in pressure. Alternatively, the capture sensor may take the form of a pair of electrodes positioned either side of the cell when in the injection position, the electrodes being able to measure changes in conductivity or permittivity or another convenient electrical or magnetic parameter. Alternatively, optical methods may be used to image the cell or detect its presence at the injection position by changes in absorbance, refractive index, light scattering and the like. In the case of a flexible needle, pressure sensors may be used to detect the presence of a cell.

It will be appreciated that, depending on the cell density, density may vary from . . . to . . . and the efficiency of injection required, it may be desirable to have a means of detecting the presence of a cell as it approaches or enters the injection area, i.e. a "cell sensor". This may be achieved by any convenient means for example by a pair of electrodes positioned either side of the cell when in the position for detection, the electrodes being able to measure changes in conductivity or another convenient electrical parameter. Alternatively, optical methods may be used to image the cell or detect its presence at the desired position by changes in absorbance, refractive index, light scattering and the like.

Optionally the device will be controlled by a "controller" which will monitor and coordinate the arrival and movement of cells in the injection unit. The controller will automatically adjust the flow of cells in the various chambers to co-ordinated the arrival of cells at the injection needle.

Velocity of the cells as an active or passive velocity will be in the order of 10 micron/sec to 10 mm/sec, preferably 100 micron/sec to 1 mm/sec A further way of impelling the cells onto the injection needle is by deflecting the flow at a substantial angle, for example between 40 degrees and 90 degrees such that the cell impacts a defined area of the channel wall which contains the injection needle. Removal of the cell is achieved by a combination of the elasticity of the cell bouncing off the wall and the flow in the microfluidic channel, optionally enhanced by a tumbling action of the cell initiated by geometric features fabricated in the channel wall. A non-limiting illustration of a device including this arrangement is shown in FIG. 5.

Figure 5:
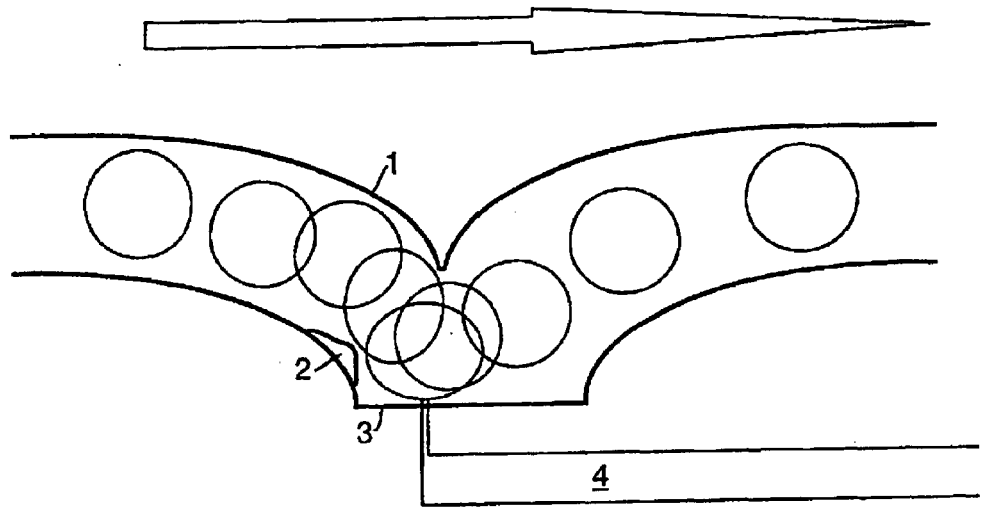
FIG. 5 is a diagrammatical view of an alternative arrangement for a cell injector.

FIG. 5—Is a diagram of a microfabricated cell injector with a conduit consisting of a single channel 1. Cells impelled through the channel are forced onto an injection needle 4 by a deflector 2. The momentum of the cell is sufficient for it to be impelled onto and then off the injection needle.

The walls of the channel are designed such that each cell is presented to the injection needle with the correct force such that the injection needle penetrates the cell wall, and that the cell then bounces off the wall and continues in the same direction down the channel, without tearing or otherwise irreparably damaging the cell wall. To achieve this, the channel walls have several features to achieve this. We here define the various surfaces and features (see FIG. 5).

a "deflector wall", which causes the liquid flow and the cells to deviate a "constrictor" which squeezes the cell slightly and increases the speed of the cell. The constrictor also encourages the cell to proceed down the channel with a tumbling action.

When the cell is positioned on the needle then injection of the material takes place. The material injected will depend on the cell type, volume and purpose of the injection. It will normally be in the range of 1% to 50% of the cell volume, for example 5% to 20%, and will typically be in the order of one or a few picolitres. Movement of the material in the injection channel may be achieved by any convenient means and may include for example a micropump or piezoelectric displacement, such as described in Transaction on Biomedical Engineering (1975) 22, 5, 424–426. The movement may optionally be continuous where it is acceptable for material to leak into the carrier fluid and where this is not economically prohibitive.

Figure 8:
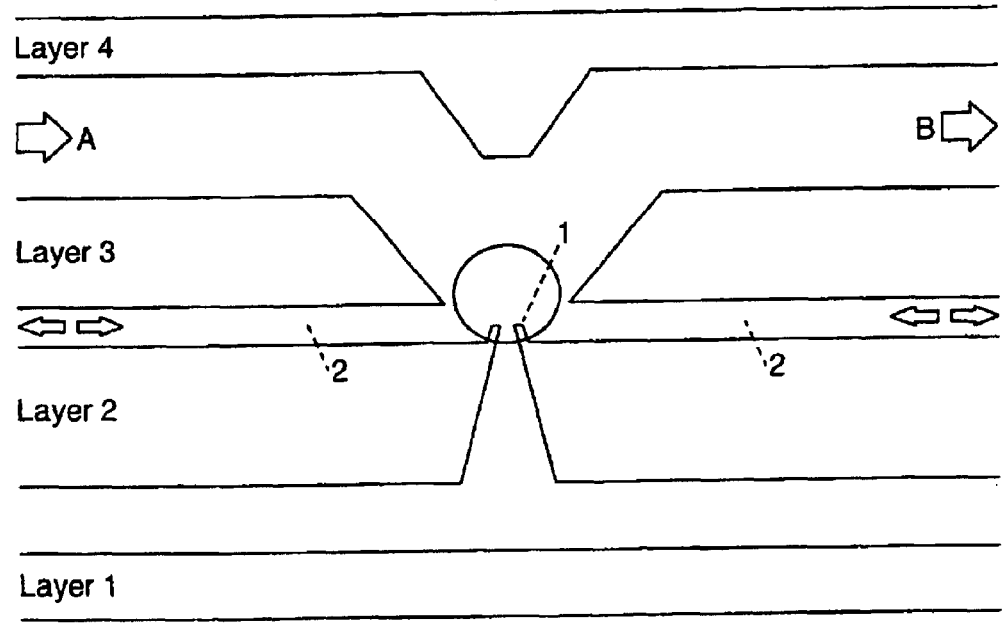
FIG. 8 is a diagrammatical view of an injection device showing the needle and housing.

Devices may be made by the use of microfabricated layers such as shown in FIG. 8. Here the cells travel in suspension down a channel defined by the gap between layers 3 and 4, and by walls perpendicular to the layers, formed from layer 3 or 4 or both. As each cell enters the injection area, flow away from the injection area is initiated in the channel formed between layers 2 and 3. This impels the cell onto the injection needle. This flow may optionally be maintained while injection takes place, whereafter the flow is reversed thereby ejecting the cell from the injection needle into the main cell flow. The main cell flow may optionally be paused or slowed while the cell is drawn onto the injection needle, is injected and released. Alternatively, the sequence of flows may be as follows: 1) channel A to channel C until a cell is detected at the injection needle 2) injection 3) channel C to channel B until cell is ejected 4) repeat i.e. go to 1). The length of step 3) will depend on experience of what is required to eject the cell and the desired concentration of the cells coming from the device, it being understood that the device could concentrate or dilute the cells depending on the relative timing of the flow steps.

The relative size and shape of the features and other aspects of the injector device will depend on numerous factors. This will include the type and size of cells being injected, the desired efficiency of injection (i.e. the percentage of cells that are successfully injected), the desired throughput, flow rate, clumping tendency of the cells and other factors.

The device may be fabricated in glass, silicon, plastic or any other suitable material or combination of materials using conventional microfabrication techniques. It will be appreciated that for each material the constraints imposed by the material and manufacturing technique used may require different geometries to those shown in the diagrams contained herein.

We have further found that microfabrication technology offers an approach to optimise the various parameters to suit the cells type and the application. At the design stage, one or more devices are fabricated that have injection areas of different geometries and different arrangements of design elements in a large number of combinations. It is then a straightforward matter to inject cell populations down the different injection areas and determine empirically which arrangement gives satisfactory results according to whatever success criteria are considered important. Furthermore this approach allows the design to be optimised for each type of cell.

FIG. 6—Shows how a number of the devices may be placed in parallel to achieve an even higher throughput. Cells are fed into the microfabricated injectors 1 by a series of splitting channels, one for each injector, and then the resulting injected cells collected from all the injectors in a collecting pool 2. The material for injection is held in a storage area 4 and pumped through to the injection needle tips by a suitable pump 3.

It will be clear to the microtechnologist that there are many possible arrangements of the conceptual and material elements of the present invention, and analogues or equivalents thereof, that may be expected to yield a device and method for achieving high throughput injection of cells.

The use of the method and device of the invention are numerous in the fields of, for example, life science research, medical research, drug and agrochemical discovery and diagnostics.

The principle advantage is that the device provides a means of reliably injecting a wide variety of material. Thus it may be used as a generic and predictable transfection method which allows genetic material to be injected into cells with high efficiency. This is of particular advantage when there is a need to transfect cells that are difficult to transfect by conventional means. It is also of advantage when it is required to transfect cells with two or more genes.

The method of the invention may also be used for validating assays used for testing modulation of a biological target. In particular, the situation often arises that the only material that can validate an assay, that is provide a control, is material that cannot be readily provided to the cell interior. The method provides a way of reliably injecting a wide variety of samples.

The device and method of the invention may also be used for validating whether a biological target does or does not influence an important cellular process. In particular the device and method allow for inhibitory antibodies and dominant negative proteins to be incorporated inside the cell in order to ascertain the relevance of target proteins, interactions, enzyme activity and pathways to potential therapeutic intervention. The device and method can therefore be used to prepare cells for a significant number of assays.

The device and method of the invention may also be used for the construction of intracellular assays: In particular, protein and other non-permeable agents or probes, in particular labelled agents or probes may be incorporated into a population of cells that may subsequently be employed for testing and evaluating compounds. In particular labelled antibodies may be injected. Probes may be based on numerous assays principles, for example fluorescence resonance energy transfer (FRET), fluorescence polarisation and fluorescence correlation spectroscopy or may be specifically designed to modulate their signal in the presence of a target molecule or enzyme activity.

The device and method of the invention may be used to evaluate compounds of pharmaceutical or agrochemical interest, especially in cases where there are concerns about the ability of the compound to penetrate the cell. The device allows all such compounds to be reliably incorporated into the cell and reach the site of action.

The device and method of the invention may be used to ascertain the sensitivity of cells to certain compounds which are injected. This will be of value in determining which compound should be employed to treat a particular condition.

The method of the invention may also be used for ex vivo therapy, for example ex vivo gene therapy. Here a population of cells from a human subject may be removed, microinjected using the device and method of the invention and replaced into the subject.

It will be clear that in many applications it is advantageous to incorporate process or analysis steps on the same device, a micro total analysis system.

Accordingly, we disclose an integrated cell process device which comprises the cell injection function, as described herein, combined with one or more process or analysis steps.

Process steps may include for example further injections or extractions, cell incubation and storage, cell fusion, FACS (fluorescence-activated cell sorting) or other cell sorting, cell lysis, selective cell lysis where certain cells are lysed but not others, or incubation with an agent (a test compound, cell stimulant, nutrient or other) or other environmental factor, such as temperature or light or use in a biological assay. The biological assay may include for example an assay for the biological activity of one or more test compounds. Such an assay may involve incubation of the cell prior to injection or after injection. Optionally the compound(s) may be allowed to contact the cell while it is on the injection needle by for example introducing the compound to the liquid passing the cell: this would allow measurements to be made on the biochemical, physical or electrical response (or any other response) as a result of the compound(s) or other stimuli.

Analysis steps may include flow cytometry, chromatography or analytical analysis of cellular contents, visualisation of cells (microscopy) The process or analysis steps may either precede or follow the injection step, or both. In the case of FACS, this may sort the cells into different channels where they are injected with a different injection material. Subpopulations may optionally be pre-marked for FACS sorting. The applications of FACS and MACS (magnetic-activated cell sorting) has been demonstrated in Telleman P.

et al. Proceedings of the µTAS'98 Workshop, Kluwer Academic Publishers 39-.

Process or analysis steps may be incorporated such that they take place either before, during of after the injection process. The sequence of steps will be apparent to the skilled person.

A further application of the invention is that it may be used as a means of extracting material from inside cells. This may be achieved by simple reversing the flow in the injection channel. This ability may be exploited either to harvest an intracellular cell product, which may be for example a protein or genetic material, or it may be used to sample cell contents for subsequent analysis.

FIG. 8—Is a diagram of a microfabricated cell injector with a conduit consisting of three parallel channels defined between 4 layers (Layers 1 to 4). Cells pass in the direction A to B in the channel defined by layer 1 and 2. An oscillating pressure is applied in the second channel 2 which impels a passing cell onto the injection needle 1 and in the opposite direction forces the cell off the injection needle and back into the flow of A to B. Alternatively the flow is from A to C until a cell is detected at the needle and then, after injection, the flow is from C to B for a period. The third and fourth layer define the internal surface of the injection needle and carries the material for injection into the cells. The injection needle has a height in the order of 3 micron above the upper surface of layer 2, the walls are approximately 1 micron thick and the internal diameter of the needle is 1 micron at its narrowest point.

In an alternative feature of the invention material is not injected into the cell but is extracted, such as parts of the cytoplasm or organelles (e.g. the nucleus or mitochondria). This alternative feature of the invention may allow for several new uses which previously have not been viable, except on a very small scale. These uses include the following:
1. Analysis of cell contents—a sample of cytoplasm, or an organelle of the cell(s) may be extracted and analysed to analyse the content of the cell (analysis of, for example, specific proteins, the proteome, metabolites or nucleic acids). This analysis may be performed before or after exposure of the cell(s) to a compound or environmental factor. Such a compound or environmental factor (such as a cytokine) may, optionally, be delivered into the cell directly by the needle prior to extraction.
2. Measuring Cell Permeation—An important factor in pharmaceutical development is to determine the availability of the compound to its biological target within the cell. By extracting samples directly from the cells direct measurements of the presence of the compound may be made. It is possible to determine the distribution of the compound within the organelles or cellular compartments of the cell. Alternatively the entire contents of a cell may be vacated and replaced by buffer solution. These empty cell sacs may be used to measure whether compounds diffuse across cellular membranes, or are actively transported, and the rate of diffusion/active transport.
3. In-cell PCR—Cell microinjection allows access to the cell interior for in-cell PCR.

The device is also able to be used to measure the electrical properties of cells for example by means of electrodes placed in the injection channel and the channel containing the cells. For example, the membrane potential and membrane permeability may be measured on populations of cells, optionally in response to external agents or test compounds.

Construction of the Devices

Microfabricated devices of the invention may be prepared by standard techniques currently employed by microtechnologists. By way of example the following suggested route for manufacture of the device in FIG. 8 is provided.

The injection needle has a height in the order of 3 micron above the upper surface of layer 2, the walls are approximately 1 micron thick and the internal diameter of the needle is 1 micron at its narrowest point.

Several methods for fabrication of the needle could be devised by a skilled technologist. For example, layer 2 could be fabricated from glass or silicon by 1) patterning to give cylindrical resist cores in the desired positions on the chip, 2) sputtering with glass or metal over the cores at an angle away from normal to cover the sidewalls, 3) planarising with resist and ion milling off the top to leave a core surrounded by an open cylinder of glass or metal, 4) removing the resist to leave a cylinder and 5) anisotropically etching from the rear to connect with the hole in the centre of the cylinder. It will be understood that other features such as channel walls, spacers, electrodes etc. will also be incorporated during the fabrication of the needle feature.

Various techniques may be employed to sharpen the tip of the injection needle to aid penetration. For example milling techniques may be employed. Alternatively, the 5-step method described above may be elaborated by the provision of a thin metal disc, of diameter slightly greater than the resist cores, positioned centrally on top of the resist cores. The sputter coating to form the sides of the cylinder is then carried out from above at an angle such that the overlap casts a "shadow" on the sides of the resist, giving a sloping internal surface with the wall tapering to the top. The metal disc and resist are then removed and the etch from the rear step carried out as before. Connections with liquid resevoirs external to the device may be made in accordance with Mourlas N. J. et al. Proceedings of the µTAS'98 Workshop, Kluwer Academic Publishers 27-, and references cited therein.

Figure 10A:
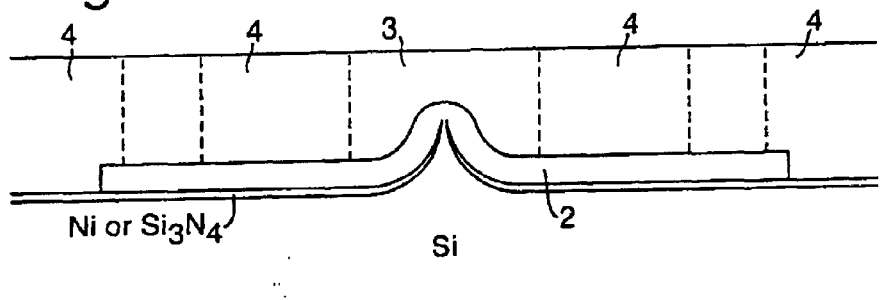
FIGS. 10 to 16 show methods to produce the devices.

Example 3 FIG. 10—Shows one of several methods that can be used to produce micro-needle structures. This particular method results in needles made of silicon nitride.
1. Deposit a silicon nitride masking layer onto a silicon wafer
2. Pattern masking layer using photolithography and plasma etching to expose areas of silicon.
3. Etch silicon using HF/HNO$_3$ isotropic etch to form points of appropriate dimensions
4. Remove silicon nitride layer
5. Deposit silicon nitride
6. Pattern masking layer on back of wafer
7. Apply a thick photo-resist layer to form to the wafer to coat most of the points
8. Remove the exposed region of silicon nitride
9. Remove the photo-resist
10. Etch the silicon using KOH anisotropic etch to form hollow needle structures In a continuation of the the above process to produce a housing to surround the needle—FIG. 10a:
11. Deposit strike layer for electroplating over the front side, resist on front side, pattern to form openings where sacrificial layer (2) will be electroplated to form suction channel
12. Plate up sacrificial layer (2) (Cu or Ni) to thickness of suction channel
13. Apply SU8 layer #1 (3) to a thickness equal to the desired depth of the trap well
14. Expose SU8 #1 (3)—hardens in exposed areas (4)—areas of trap well and vias from suction channels to suction inlets are masked but not developed away.

Figure 10B:
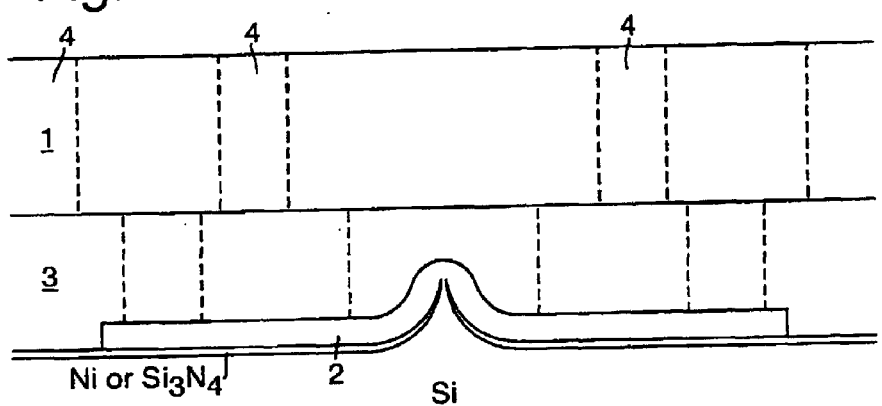
Figure 10C:
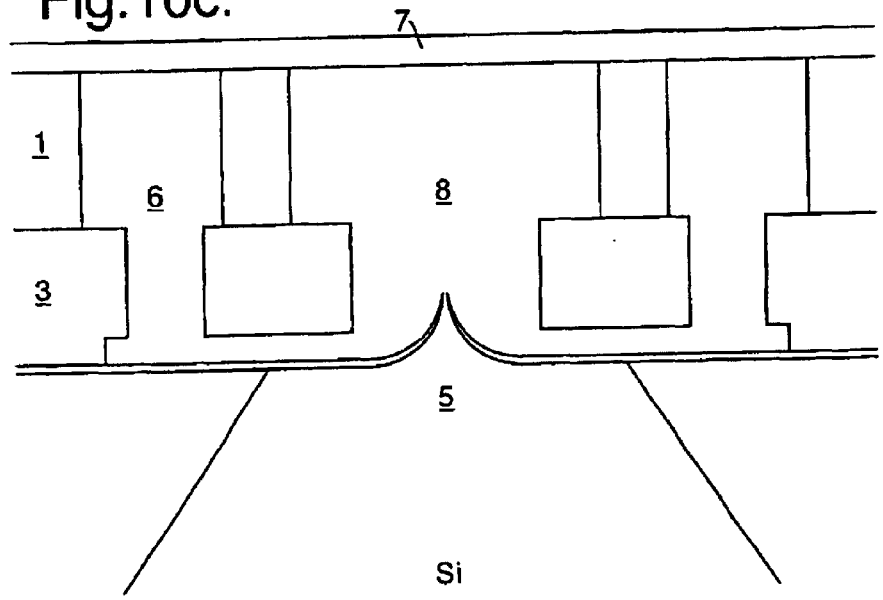

Referring to FIG. 10b:

15. Apply SU8 layer #2 (1) to define cell inlet and suction inlet. Expose (4) to pattern channels Referring to FIG. 10c:

16. Develop both layers of SU8, (1) and (3)
17. Etch the silicon from the rear side (5) only in KOH to open the cell inlet channel via to the needle, and make the needle hollow. The front side should be protected during this process. The sacrificial layer (2) is left in place to protect the Cu/SU8 interface from the KOH.
18. Remove sacrificial layer (2) to open suction channel
19. Seal transparent top cap [such as a glass cover slide] to structure to close cell (8) and suction inlets (6)
20. Seal rear cover layer to form injection channel inlets.

1 Down-hole Sputtered Needle Process

Figure 11A:
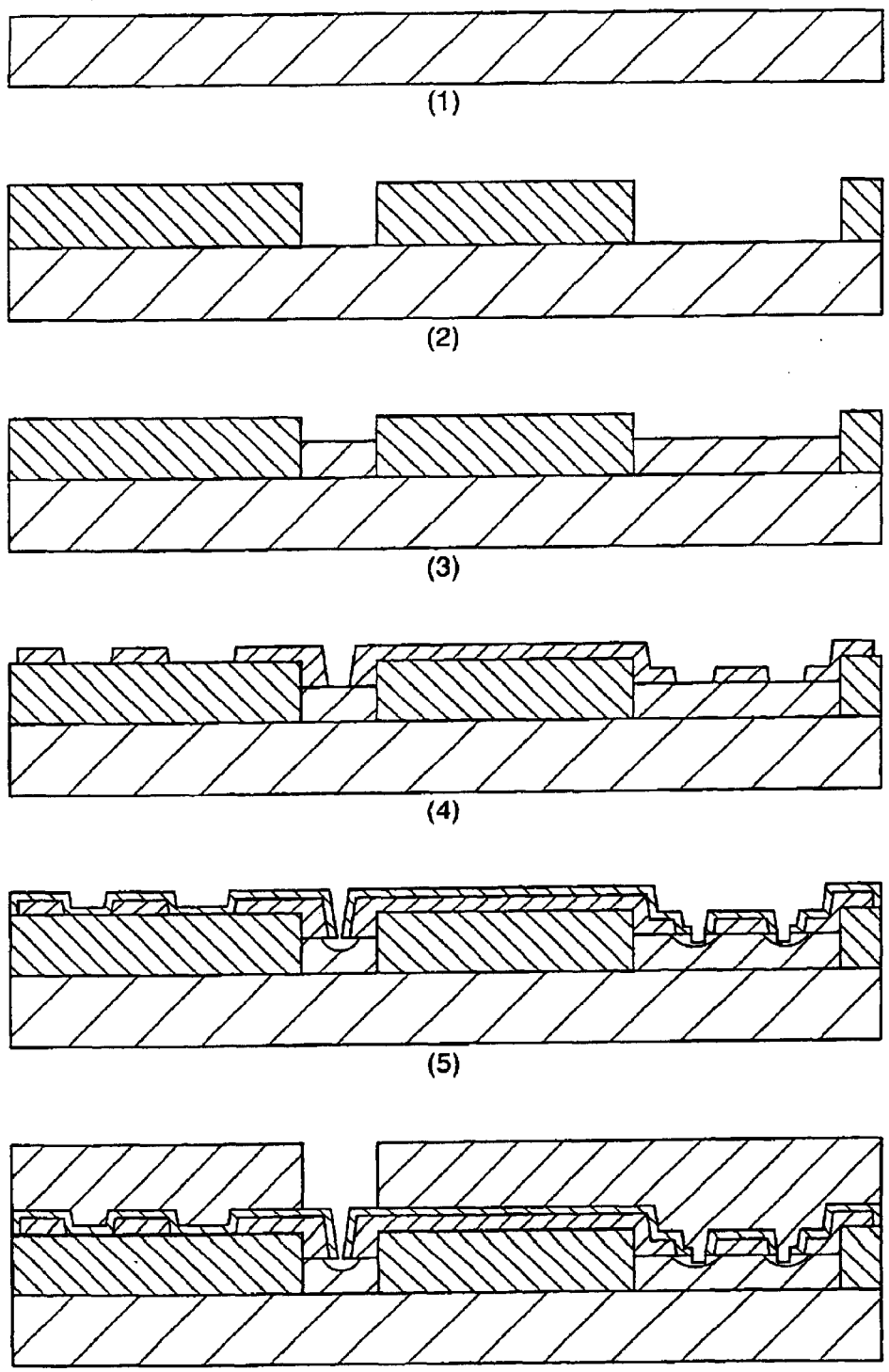

1 Start with dissolvable substrate (copper sheet, flattened)—FIG. 11a(1)
2 Spin on SU8 to depth for wells (20–30 micron).
3 Expose using mask SU8-1b and develop to produce wells and openings for via to "suck" channel connection—FIG. 11a(2)
4 Plate up copper to part fill well so that depth sets needle tip position—FIG. 11a(3)
5 Spin on positive resist (thick enough to form suck channel over flat areas—around 3 microns, but considerably deeper in well).
6 Expose using Cu Mask so that "needle hole" is near centre of well. Alignment to ~5 micron is acceptable.
7 Develop. Heat to soften resist and round edges—FIG. 11a(4)
8 Expose to copper etch sufficient to remove ~1–5 micron of copper at openings in resist to produce undercut.
9 Sputter on needle wall forming film e.g. SiO2 or glass to ~1 micron on level areas FIG. 11a(6)
10 Spin Su8 (~10 to 30 micron) and expose using Cap Mask aligned so that cap features are directly above needle holes. Alignment accuracy better than ~7 micron is acceptable.
11 Develop to open port behind injection needle structure—FIG. 11a(5)
12 Take glass sheet with sawn channel (0.5 to 5 mm wide) for injection supply and align and stick this onto coated substrate using adhesive (e.g. epoxy, UV cure acrylic, 3M self adhesive films)—FIG. 11b(7)
13 Dissolve original (copper) substrate.
14 Inverting to use glass sheet as lower level of substrate, spin on SU8 (~50 micron) and expose using mask SU8 2 with reversed symmetry to form cell feed and solution suck channels. Alignment to 10 micron is acceptable.
15 Cap with glass sheet coated with adhesive (e.g. as above in 12). Glass sheet should have pre-cut or etched channels to allow connection of tubes—FIG. 11b(8)

Horizontal Needle Method

Figure 12A:
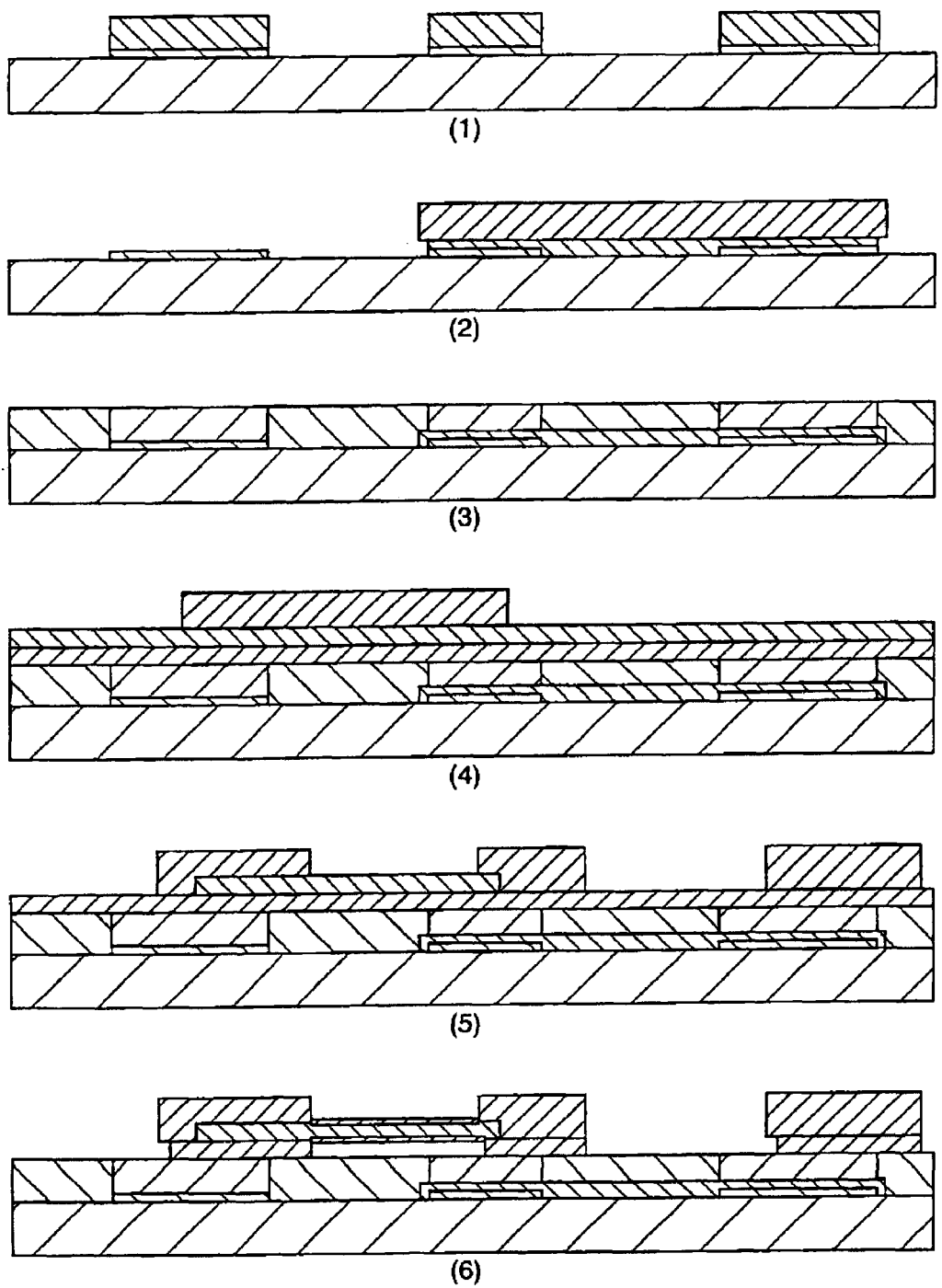

1 All over one surface of flat transparent substrate (glass, Silica or possibly polymer) deposit opaque metal insoluble in Copper etch (e.g. Ni, Al, Cr).
2 Spin on positive resist (thin), and expose using mask SU8 1b. Develop pattern and etch the metal—FIG. 12a(1)
3 All over substrate deposit/plate copper to thickness required for suck channel (~3 micron).
4 Spin on positive resist. Expose using Cu Mask. Align so that needle point hole in Cu is in centre of metal circle corresponding to well. Alignment to 5 micron is acceptable. Develop. Etch copper to form rectangles—FIG. 12a(2)
5 Remove positive resist and spin on SU8 to ~half depth required for wells (10–15 micron).
6 Expose using Mask SU8 1b so that wells align with "needle position hole" in Cu, and so via for suck channel is over other end of Cu rectangle. Alignment not critical, but should be not more than 10 micron misalignment. Leave undeveloped see FIG. 12a(3)
7 Coat all over with sacrificial metal (Ag, Cu, Zn) to ~1 to 3 micron.
8 Coat all over with needle core metal (Al, Ni) (# 1–3 micron).
9 Spin on positive resist. Expose with mask having narrow (1–3 micron) dark bars. This can probably be on Cap Mask. Thin bar should be aligned to centre of well ("needle position hole") so that bar extends over half way across well. Alignment to ~5 micron may be required—FIG. 12a(4)
10 Needle core metal is etched to form bar without etching the sacrificial metal.
11 Positive resist is removed. Positive resist is spun on and exposed using Mask SU8 1b displaced from previous position by amount which defines projection length of final needle (3–15 micron). The resist is developed—FIG. 12a(5)
12 The sacrificial metal layer is etched without etching the needle core metal leaving the needle core metal bar as a bridge with ends covered with positive resist.
13 The needle core metal is treated by oxidation, anodisation, or plating to form an insoluble coating on the exposed surfaces—FIG. 12a(6)
14 The substrate is coated with SU8 to a thickness to form the top half of the well structure (10–15 micron), and exposed using mask SU8 1b Alignment of well centre probably needs to be to 5 micron or better, depending on how long needle projection is set. Also invert substrate and expose without mask through substrate to harden SU8 under part of bar—FIG. 12b(7)
15 Spin on SU8 to thickness for feed channels (~50 micron) and expose using Mask SU8 2. Alignment error of up to 10 micron is acceptable FIG. 12b(8)
16 Develop through three SU8 layers—FIG. 12b(9)
17 Dissolve/etch positive resist, sacrificial metal in openings, and copper between well and needle suck via third well—FIG. 12c(10)
18 Dissolve out needle core metal. Dissolve out opaque metal films on substrate if required.
19 Stick adhesive coated glass sheet on top to enclose channels. Sheet should be pre-cut or etched to form entrances for attaching tubes—FIG. 12c(11).

Figure 13:
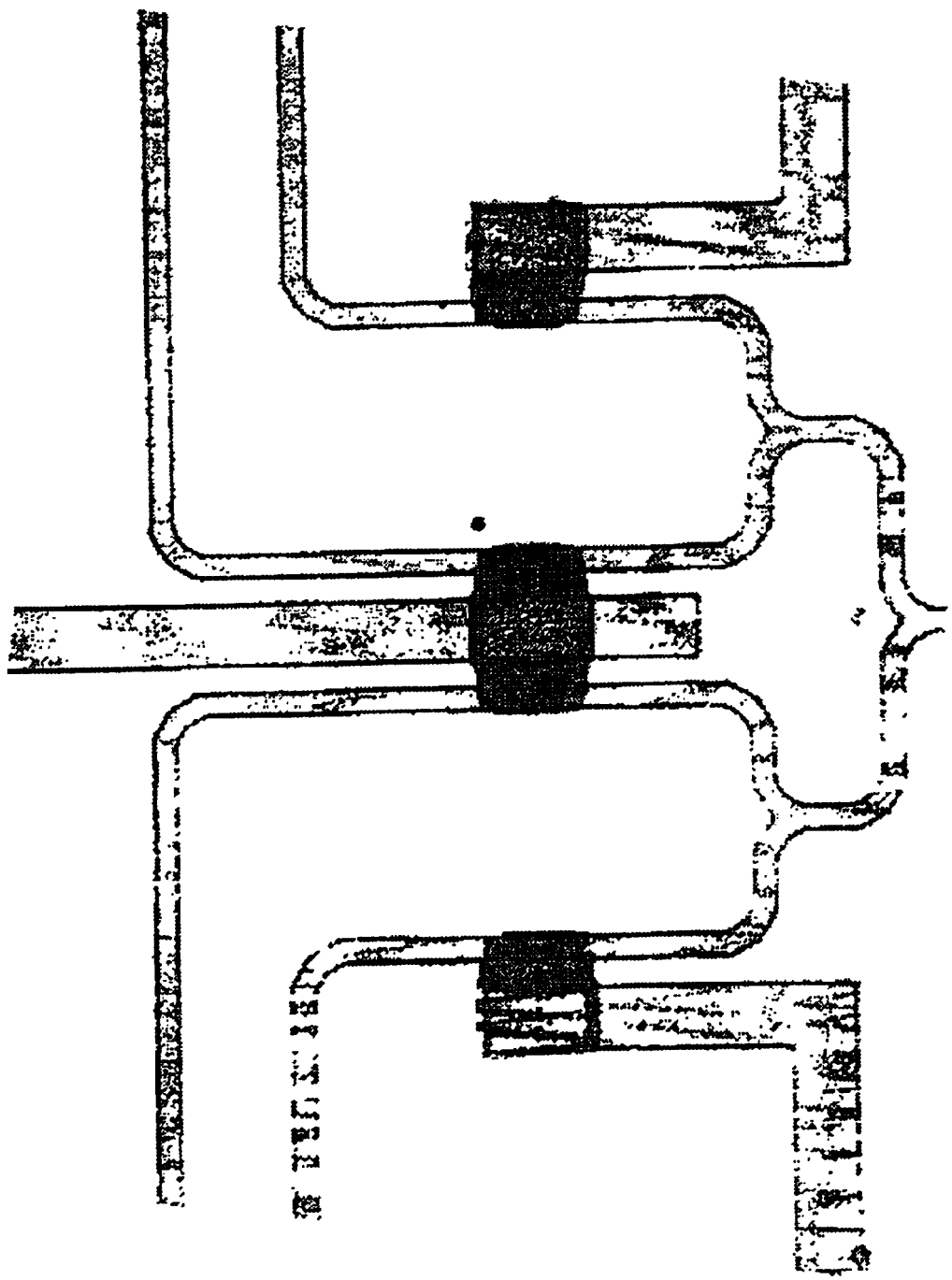
Figure 14:
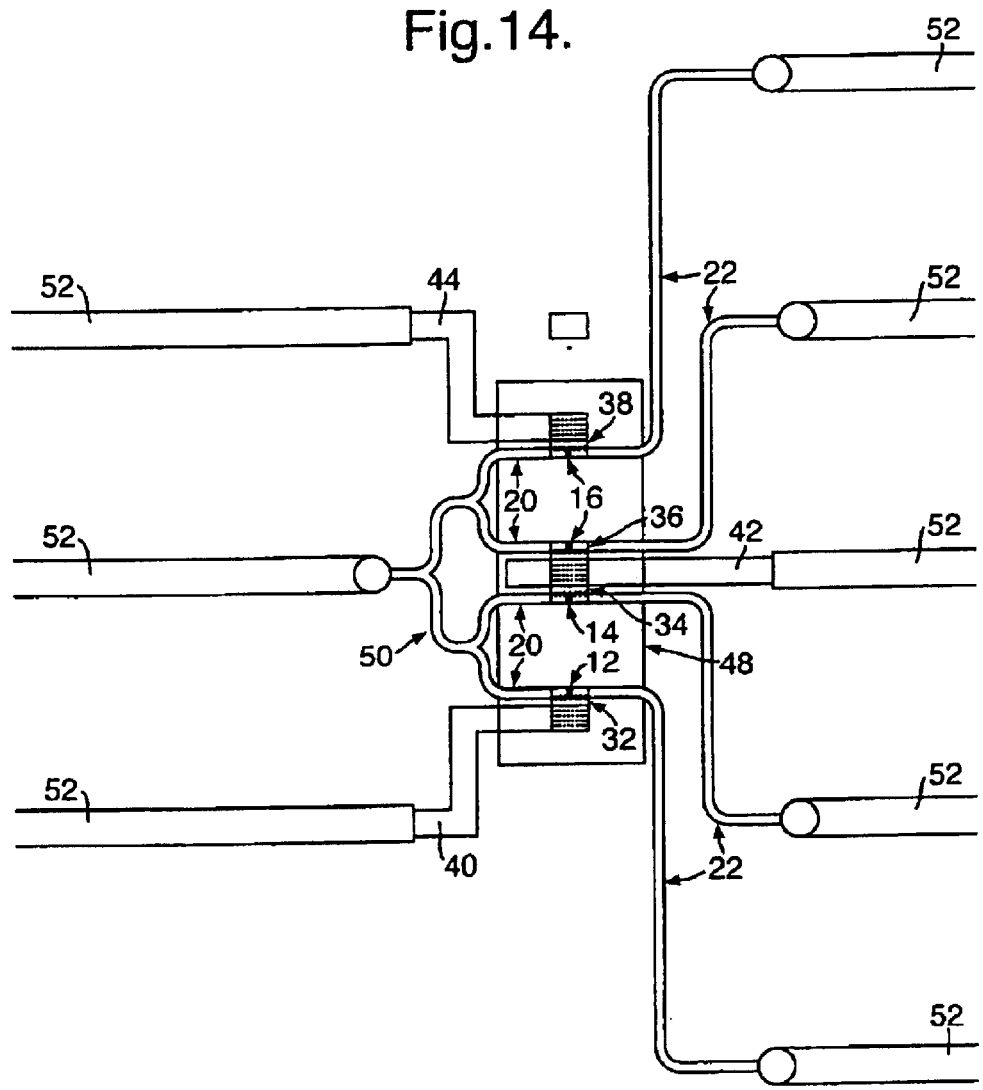

FIG. 13 is a photograph of the device of FIG. 14

FIG. 14 shows a plan view of a cell injection device fabricated according to the method of example 3 in which a device has 4 injection positions 12–18 at which cells are to be injected. Although four injection positions and associated channels are shown it is understood that the general features of the device in FIG. 14 are capable of extension to more than 4 positions with suitable layout of the device. Each injection position has an inlet channel 20 and an outlet channel 22. Also provided is a suction channel 32–38 which communicates with a trap well (not shown) at each injection position, which trap well acts to channel flow from the inlet channel to the suction channel, thereby directing cells in the inlet channel in the vicinity of the injection position into the trap well. Positioned within the trap well is an injection needle (not shown), which injects the cells when they reach the correct position in the trap well. The suction channels communicate also with a suction port 40, 42, 44, through which flow can be established in either direction. When the cell is to be trapped and injected, flow is directed from the inlet channel towards the suction port; when the cell is to be ejected from the trap well, the flow is reversed. The injection needles communicate with an injection channel through which material flows to and/or from the needle. In the embodiment in FIG. 14 the injection channel is common to all four needles, though separate injection channels might be provided. The injection channel is in the form of a via through the thickness of the device; the outline of the injection via on the rear of the device is shown at 48. The via communicates with an injection port on the rear of the device which carries injection material to and/or from the via. In the embodiment in FIG. 14 the suction channels 32 and 38 are shown each to communicate with one suction port; suction channels 34 and 36 communicate with a common port 42. Variations of connections of the inlet, outlet and suction ports are possible where a variety of degrees of commonality between them are envisaged. In the embodiment in FIG. 14 the inlet channels communicate with the branching 'binary division' arrangement 50, which serves to divide a flow of cells entering from the left in FIG. 14 into four statistically even flows, one through each of the inlet channels 20. The inlet and outlet and suction ports are terminated by broadened sections 52 into which capillary connections may be sealed allowing connection to flow systems off the device.

Dimensions of the device are chosen to suit the type of cell or other object to be injected but will typically be between 5 and 200 $\mu$m across for the inlet and outlet channels and the suction port. The trap well diameter will be between 1× and 2× the diameter of the object to be injected. If the object is deformable the trap well diameter may be less than the diameter of the object. The suction channel dimensions will be such as to prevent passage of the object from the trap well into the suction channel and so at least one dimension of the suction channel will be less than the minimum dimension of the object; substantially less in the case that the object is deformable. In the embodiment shown in FIG. 14 the inlet and outlet channels are 40 $\mu$m wide by 25 $\mu$m deep; the suction port is 100 $\mu$m wide by 25 $\mu$m deep; the trap well is 25 $\mu$m diameter by 25 $\mu$m deep and the suction channel is 150 $\mu$m wide by 3 $\mu$m deep. These dimensions are optimised to trap and inject substantially spherical objects between 12 and 25 $\mu$m diameter.

Figure 15:
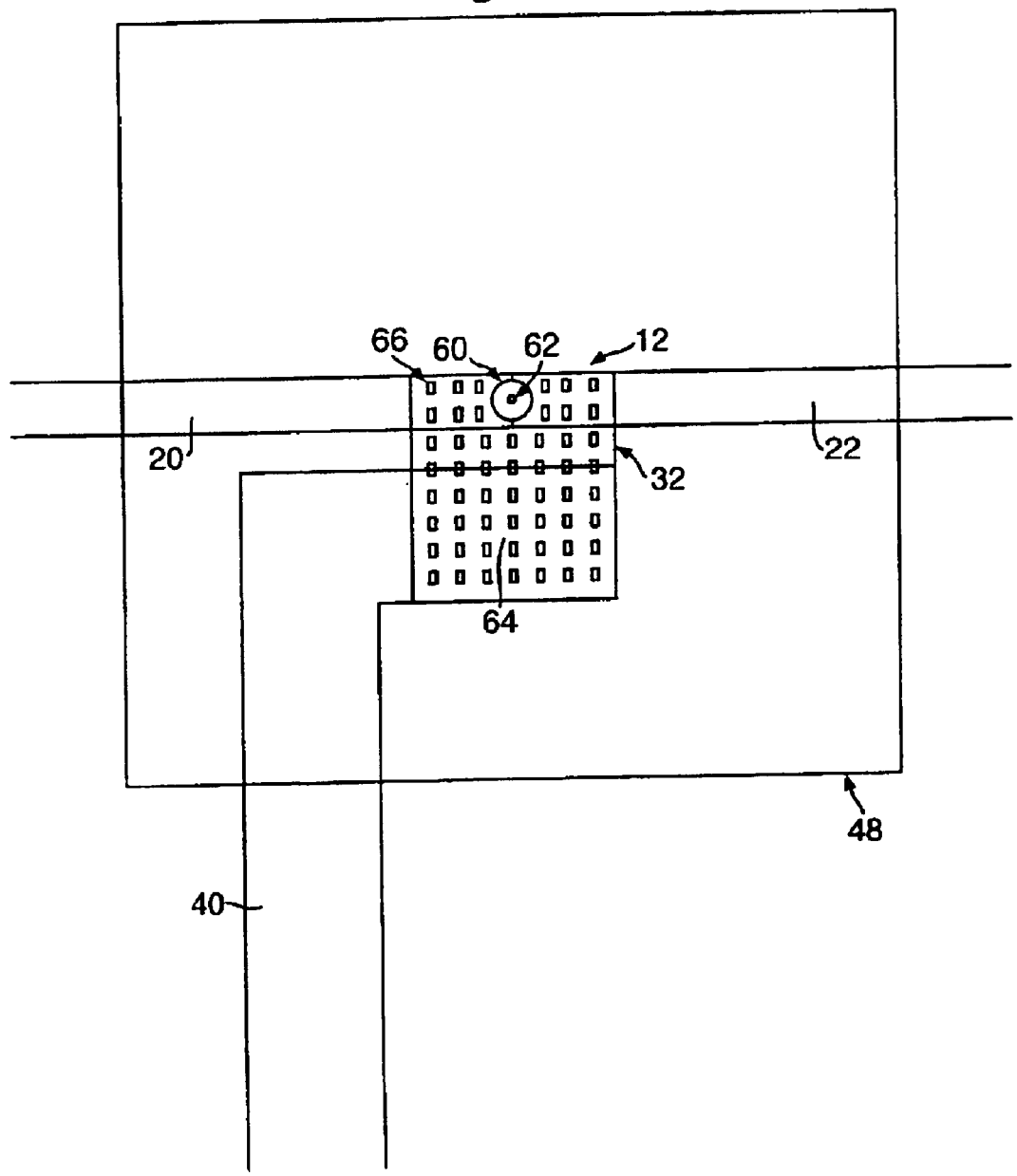

FIG. 15 shows a more detailed view of one of the injection positions 12 in an injection device of the invention, with the same nomenclature as FIG. 14. The trap well 60 is shown with the injection needle 62 in the base of the well. The fluid flow paths in the device are from inlet channel 20 to outlet channel 22 to introduce objects to be injected into the device; from the inlet channel down through trap well 60, surrounding needle 62, through suction channel 32 and up through via 64 into suction port 40. Supports 66 are provided to hold the structure defining the floor of the inlet channel 22 above the roof of the suction channel 32 above the floor of the suction channel, while allowing unimpeded flow through the suction channel.

Figure 16:
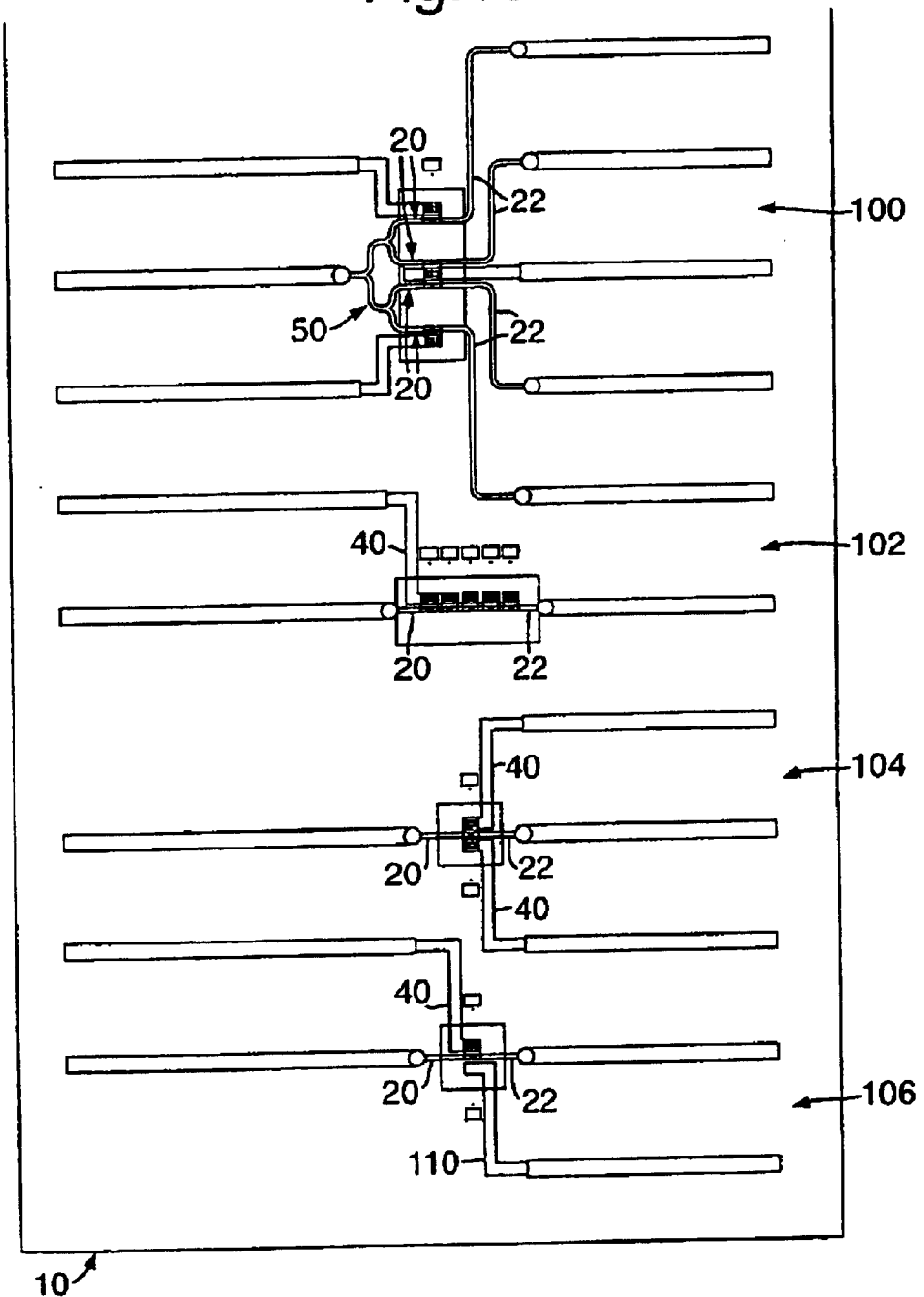

FIG. 16 shows an overall plan view of a chip comprising several injection devices of the invention of different configurations. Chip 10 has on it injection devices 100–106, each separately operable and intended to demonstrate various possible configurations of serial and parallel operation of injection. Device 100 is as shown in FIG. 14. Device 102 has five injection positions in series with common inlet and outlet channels, common suction port and common injection channel. Device 104 has a single injection position and two suction ports to give even and symmetrical suction flow around the object to be injected in the vicinity of the trap well. Device 106 has a single injection position and a single suction port, and is as shown in greater detail in FIG. 15. The additional structure 110 shown as part of device 106 is a dummy channel which might be used to communicate with the trap well for purposes such as addition of material into the well in the intimate vicinity of the cell, for example to test cell responses to compounds while in-situ on the needle.

The devices shown in FIGS. 14–16 are all operated by external sources of fluids and driving force, for instance pressure and/or vacuum. Control means (not shown) for controlling such driving forces might be external to the devices are integrated wholly or partially with them; for instance micropumps might be integrated onto the device. It is understood that electrodes might be integrated onto the devices in ways known in the art, in order to provide either driving force for fluids, e.g. by electro-osmotic flow, or for cells or other objects, e.g. by dielectrophoresis, or to provide sensing of the position or electrical potentials associated with cell physiology or other properties of objects. The electrodes might also provide sensing or control functions for fluids surrounding the cells or objects.

Figure 17:
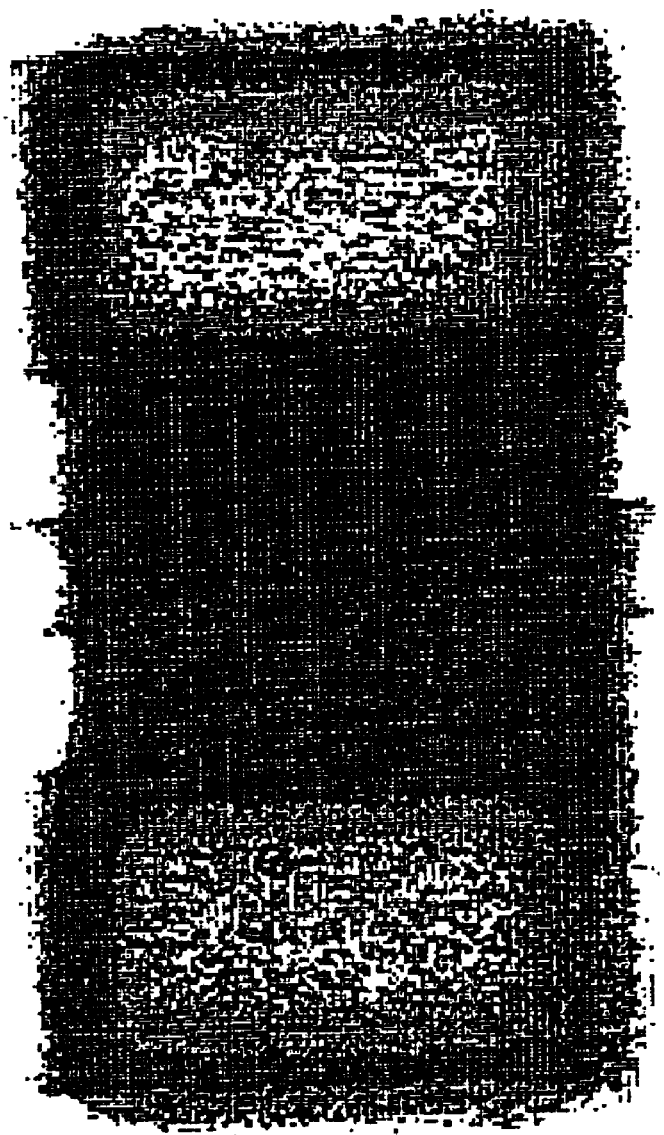
FIG. 17 is a close-up picture of an injection device as shown diagrammatically as item 104 in FIG. 16.

FIG. 17 shows a close-up picture of an injection device as shown diagrammatically as item 104 in FIG. 16, fabricated by the integrated process [example 3 above] in SU8 photo-patternable epoxy on an Si chip. The inlet and outlet channels are shown with the trap well leading down from them into the device. Two suction ports are provided, one each side of the inlet and outlet channels. The injection needle is situated at the bottom of the trap well and appears as a small light dot. The small size of the needle (12 $\mu$m in height, 2 $\mu$m across at the top) makes it hard to image in the depth of the trap well, which is 50 $\mu$m deep from the top surface of the device, 25 $\mu$m deep below the floor of the inlet and outlet channels. The microscope is focused at the level of the top of the needle, so the details of the suction channels are indistinct.

Other dimensions of the parts of the image are: inlet and outlet channels, 40 $\mu$m wide by 25 $\mu$m deep; trap well 25 $\mu$m diameter by 25 $\mu$m deep above the base of the needle; needle: 12 $\mu$m high above the base, 2 $\mu$m diameter, 0.1 $\mu$m needle material thickness, as shown in FIG. 9. Suction channel: 4 $\mu$m high above the base of the needle, 150 $\mu$m wide.

FIG. 13—Shows a general view of an injection device as shown diagrammatically in FIG. 14 and as item 100 in FIG. 16, fabricated by the integrated process as for FIG. 17. The inlet channels to the four injection positions are fed from a common inlet port via a binary division tree; the outlets go to separate ports in this design. The features of the device are as described for FIG. 14. Dimensions of the various parts are as above. Slight cracks are visible at the corners of some of the channels. these arise from stress in the SU8 layers used to form the microchannels and do not affect the working of the device or the integrity of the structure.

What is claimed is:

1. A microfabricated cell injector comprising an internal surface defining a conduit for transporting cells suspended in a fluid, the conduit having an inlet and an outlet, the conduit further comprising a cell injection needle for piercing cells, such that, in use cells enter the injector via the inlet, are moved along the conduit and are pierced by the cell injection needle whereupon material is (1) injected into the cell, (2) extracted from the cell, or (3) injected into the cell and then extracted from the cell the steps being in any order and any number of times, and the cells are then moved to the outlet.

2. A microfabricated cell injector as claimed in claim 1 where the needle is a hollow structure and injection or extraction is actuated by a cell sensor at an injection area which determines the presence of a cell on or nearby the needle.

3. A microfabricated cell injector as claimed in claim 1 which additionally comprises a cell capture sensor at an injection position which determines the presence of a pierced cell on the injection needle and actuates injection of material into the cell or extraction of material from the cell.

4. A microfabricated cell injector as claimed in claim 3 wherein the cell capture sensor prevents further cells being impelled towards the needle.

5. A microfabricated cell Injector as claimed in claim 3 wherein the cell capture sensor actuates the expulsion of the cell from the needle after injection of the material into the cell or extraction of material from the cell.

6. A microfabricated cell injector as claimed in claim 1 wherein the needle is solid and material for injection is present within the fluid suspending the cells.

7. A microfabricated cell injector as claimed in claim 1 wherein the needle is a non-cell piercing hollow structure and cell piercing is achieved by a cell disrupting chemical or force being applied through the end of the non-cell piercing needle structure.

8. A microfabricated device containing a plurality of cell injector units as claimed in claim 1 wherein the respective inlets and outlets of the cell injecting units being each connected such that the cells are divided into each injector unit and recombined after injection.

9. A method for the microinjection of cells which method comprises passing a suspension of cells in a fluid through a conduit, the conduit comprising an inlet and an outlet, the cells entering the conduit via the inlet, the conduit further comprising a cell injection needle, the cells thereby being pierced by the injection needle and material is: (1) injected into the cell (2) extracted from the cell or (3) injected into the cell and then extracted from the cell the steps being in any order and any number of times; as the cells pass through the conduit, and moving the cells to the outlet.

* * * * *